US00PP34445P2

(12) United States Plant Patent
White

(10) Patent No.: US PP34,445 P2
(45) Date of Patent: Jul. 26, 2022

(54) ***TRADESCANTIA* PLANT NAMED 'TPIWH01-0'**

(50) Latin Name: ***Tradescantia flumiensis* fo. *albovittata***
Varietal Denomination: 'TPIWH01-0'

(71) Applicant: Amelia White, Charleston, SC (US)

(72) Inventor: Amelia White, Charleston, SC (US)

( * ) Notice: Subject to any disclaimer, the term of this patent is extended or adjusted under 35 U.S.C. 154(b) by 0 days.

(21) Appl. No.: 17/474,519

(22) Filed: Sep. 14, 2021

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
See application file for complete search history.

(56) References Cited

PUBLICATIONS

Tropicos.org. Missouri Botanical Garden. Nov. 2, 2021 <https://tropicos.org/name/100501960> citation for *Tradescantia* (1 page total).*

* cited by examiner

*Primary Examiner* — Susan McCormick Ewoldt
(74) *Attorney, Agent, or Firm* — Cassandra Bright

(57) ABSTRACT

A new and distinct cultivar of *Tradescantia* plant named 'TPIWH01-0' is disclosed, characterized by strong white variegation covering between 30% to 60% of the leaf blade. Plants of the new variety show excellent vigor under varying light conditions. The new variety is a *Tradescantia*, typically used as an ornamental plant.

2 Drawing Sheets

Latin name of the genus and species: *Tradescantia flumiensis* fo. *albovittata.*
Variety denomination: 'TPIWH01-0'.

BACKGROUND OF THE INVENTION

The new cultivar is a product of chance discovery. The new variety was selected as a naturally occurring single branch mutation of an unnamed, unpatented variety of *Tradescantia flumiensis* fo. *albovittata*. The discovery was made by the inventor, during Spring of 2020 in a private garden in Charleston, S.C.

Plants from this initial selection were grown and assessed for stability in Santa Paula, Calif. Asexual reproduction of the new cultivar 'TPIWH01-0' by terminal cuttings was first performed in Santa Paula, Calif. at a commercial greenhouse during the Summer of 2020 and has shown that the unique features of this cultivar are stable and reproduced true to type through successive generations.

SUMMARY OF THE INVENTION

The cultivar 'TPIWH01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TPIWH01-0'. These characteristics in combination distinguish 'TPIWH01-0' as a new and distinct *Tradescantia* cultivar:

1. Strong white variegation covering between 30% to 60% of the leaf blade.
2. Excellent vigor under varying light conditions.

PARENT COMPARISON

Plants of the new cultivar 'TPIWH01-0' are similar to plants of the parent variety in most horticultural characteristics, however, plants of the new cultivar 'TPIWH01-0' differ from in the following characteristics:

1. The new variety consistently produces leaves with more white variegation than the parent variety.
2. The new variety has not been observed to blush pink or lavender under varying light or temperature conditions, as observed in the parent variety.

COMMERCIAL COMPARISON

Plants of the new cultivar 'TPIWH01-0' are similar to plants of the commercial variety *Tradescantia caperata* 'Nanouk', U.S. Plant Pat. No. 29,711. However, plants of the new cultivar differ in the following characteristics:

1. The new variety has not been observed to blush pink or lavender under varying light or temperature conditions, as observed in the variety 'Nanouk'.

Plants of the new cultivar 'TPIWH01-0' are similar to plants of the unpatented *Tradescantia* 'Variegated' grown commercially. However, plants of the new cultivar differ in the following characteristics:

1. The new variety has larger foliage than this comparator.
2. Leaves of the new variety have white and green variegation; this comparator has yellow and green variegation.

BRIEF DESCRIPTION OF THE PHOTOGRAPHS

Figure 1:
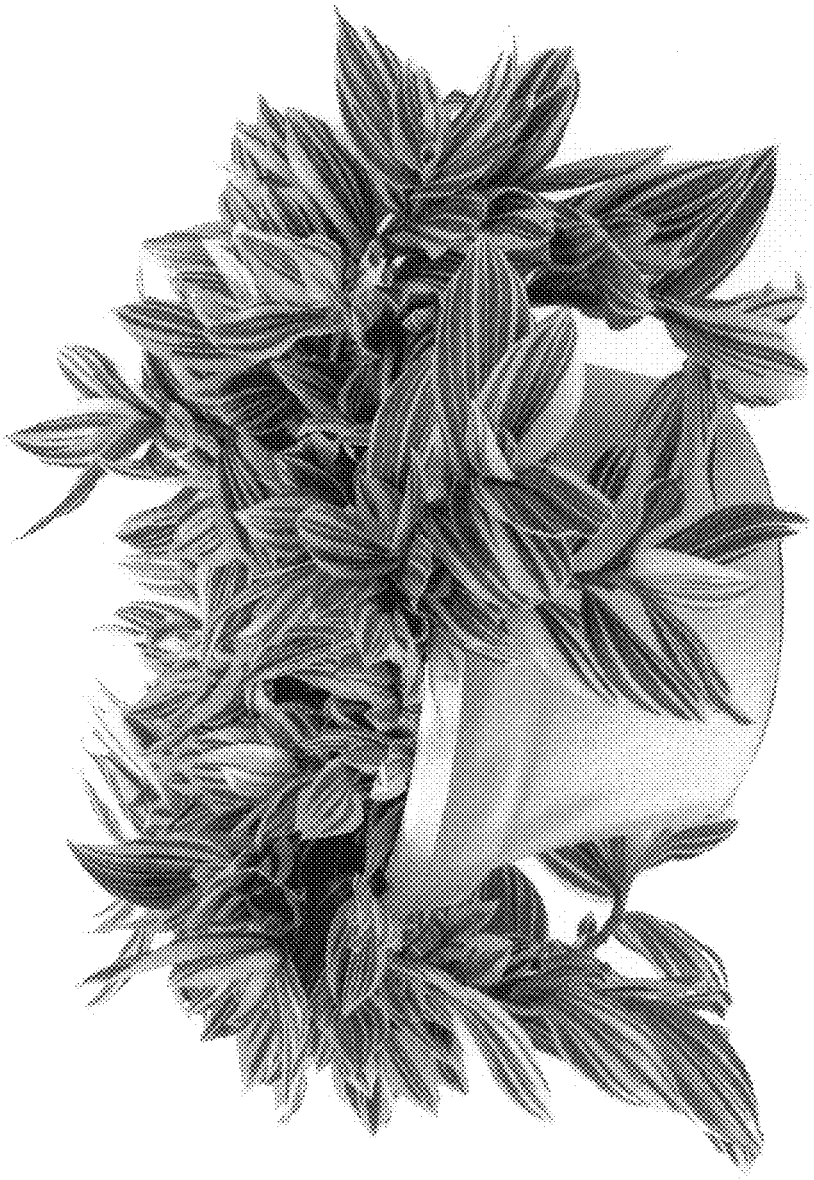

The accompanying photograph in FIG. 1 illustrates in full color a typical plant of 'TPIWH01-0' grown in a greenhouse in Santa Paula, Calif. The plant is approximately 20 weeks of age.

Figure 2:
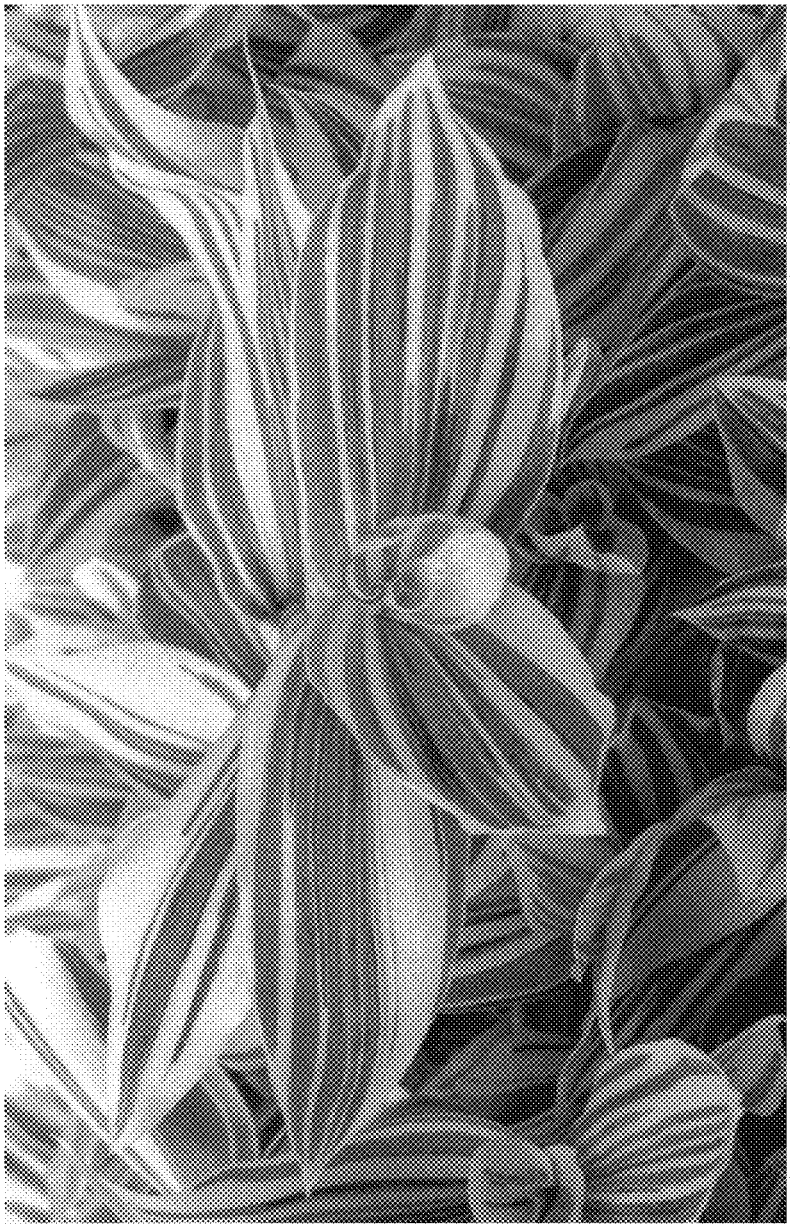

FIG. 2 illustrates a close up of the foliage. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TPIWH01-0' plants at 22 weeks of age, grown in a commercial controlled greenhouse in Santa Paula, Calif. Measurements and numerical values represent averages of typical types.

Botanical classification: *Tradescantia flurniensis* fo. *albovittata* 'TPIWH01-0'.

PROPAGATION

Time to initiate roots: About 10 days at approximately 20° C. in Summer.

Description of roots: Herbaceous, fine, moderately dense, freely branching. Occurring at most nodes over time. White in color, not accurately measured with RHS chart.

PLANT

Plant type: Trailing, tender foliage plant.
Pot size of plant described: Approximately 25 cm.
Growth habit: Trailing tender foliage plant.
Height: Approximately 10 cm from soil line.
Plant spread: Approximately 45 cm.
Growth rate: Moderate.
Branching characteristics: Very freely forming lateral branches.
Diameter of stem: Approximately 5 mm.
Texture of stem: Glabrous.
Color of stem: Near RHS Green 138A. Flushed 138C near nodes.
Stem strength: Very flexible, not easily broken.
Number of leaves per stem: Average 12 per 30 cm of stem.

FOLIAGE

Leaf:
- *Arrangement.*—Alternate.
- *Average length.*—Approximately 7.5 cm.
- *Average width.*—Approximately 3.0 cm.
- *Shape of blade.*—Moderately broad elliptic.
- *Aspect.*—Very slight undulation.
- *Apex.*—Acute.
- *Base.*—Tapered.
- *Attachment.*—Sessile.
- *Margin.*—Entire.
- *Texture of top surface.*—Glabrous.
- *Texture of bottom surface.*—Glabrous.
- *Color.*—Young foliage upper side: Near RHS White 155C, streaked Green 138A and 137C. Streaking is long, covering 90 to 100% of the leaf blade and of irregular width, with an average width of 4 to 9 mm. Both colors of Green 138A and 137C can occur on the same streak. Young foliage under side: Near RHS White 155C, streaked Green 138A. Streaking is long, covering 90 to 100% of the leaf blade and of irregular width, with an average width of 4 to 9 mm. Mature foliage upper side: Near RHS White 155C, streaked Green 138A and 137C. Streaking is long, covering 90 to 100% of the leaf blade and of irregular width, with an average width of 4 to 9 mm. Both colors of Green 138A and 137C can occur on the same streak. Mature foliage under side: Near RHS White 155C, streaked Green 138A. Streaking is long, covering 90 to 100% of the leaf blade and of irregular width, with an average width of 4 to 9 mm.

Venation:
- *Type.*—Pinnate.
- *Color.*—Indistinguishable from leaf blade.

Sheath (if present):
- *Average length.*—Approximately 5 to 7 mm.
- *Average width.*—Approximately 9 mm.
- *Color.*—Near RHS White 155C, streaked Green 138A.
- *Texture.*—Glabrous.
- *Other distinguishing characteristics.*—Roots at every node with maturity. Roots fibrous. About 2 mm thick, colored near Greyed-Orange 165A.

FLOWER

No flowers observed to date.

OTHER CHARACTERISTICS

Seeds and fruits: None observed to date.

Disease/pest resistance: No increased nor decreased resistance nor susceptibility to normal diseases and pests of *Tradescantia* has been observed.

Temperature tolerance: Tolerates temperatures from approximately 7° C. to 35° C.

What is claimed is:

1. A new and distinct cultivar of *Tradescantia* plant named 'TPIWH01-0' as herein illustrated and described.

* * * * *